(12) United States Patent
Rubinsky et al.

(10) Patent No.: US 10,094,030 B2
(45) Date of Patent: Oct. 9, 2018

(54) DEVICES AND METHODS FOR ELECTROLYTIC PRODUCTION OF DISINFECTANT SOLUTION FROM SALT SOLUTION IN A CONTAINER

(71) Applicant: Tipul Biotechnology, LLC, El Cerrito, CA (US)

(72) Inventors: Liel Rubinsky, El Cerrito, CA (US); Brian Patrick, Millbrae, CA (US)

(73) Assignee: Tipul Biotechnology, LLC, El Cerrito, CA (US)

( * ) Notice: Subject to any disclaimer, the term of this patent is extended or adjusted under 35 U.S.C. 154(b) by 20 days.

(21) Appl. No.: 15/014,940

(22) Filed: Feb. 3, 2016

(65) Prior Publication Data
US 2016/0222526 A1    Aug. 4, 2016

Related U.S. Application Data

(60) Provisional application No. 62/111,304, filed on Feb. 3, 2015.

(51) Int. Cl.
| | |
|---|---|
| *C25B 1/26* | (2006.01) |
| *C25B 15/02* | (2006.01) |
| *C25B 11/02* | (2006.01) |
| *C25B 11/04* | (2006.01) |

(Continued)

(52) U.S. Cl.
CPC .................. *C25B 1/26* (2013.01); *C25B 9/06* (2013.01); *C25B 11/02* (2013.01); *C25B 11/0405* (2013.01); *C25B 11/0415* (2013.01); *C25B 11/0431* (2013.01); *C25B 11/0473* (2013.01); *C25B 11/12* (2013.01); *C25B 15/02* (2013.01)

(58) Field of Classification Search
CPC .. C25B 1/26; C25B 9/06; C25B 11/02; C25B 11/0405; C25B 11/0431; C25B 11/0473; C25B 11/12; C25B 15/02; C25B 1/00; C25B 1/265; C25B 11/04; C25B 9/00
USPC .......................................... 204/242; 205/500
See application file for complete search history.

(56) References Cited

U.S. PATENT DOCUMENTS

| | | | | |
|---|---|---|---|---|
| 3,308,955 A | * | 3/1967 | Robarge .................. | C02F 1/686 137/624.13 |
| 3,479,275 A | | 11/1969 | Gwinn | |
| 4,561,445 A | | 12/1985 | Berke et al. | |

(Continued)

FOREIGN PATENT DOCUMENTS

| | | |
|---|---|---|
| JP | 2004181441 | 7/2004 |
| JP | 2007269325 | 10/2007 |
| JP | 201497461 | 5/2014 |

OTHER PUBLICATIONS (Paramedicine.com) Normal Saline Solution. 2009. [Retrieved on Mar. 30, 2016]., Retrieved from the Internet: URL: <http://www.paramedicine.com/pmc/Normal_Saline_Solution.html>; p. 1, "indications" section, 2009.

(Continued)

*Primary Examiner* — Ciel P Thomas
(74) *Attorney, Agent, or Firm* — Dorsey & Whitney LLP

(57) ABSTRACT

Examples described herein include electrolysis devices for producing a disinfectant solution from a salt solution in a container and methods of using the same. The devices include an electrode assembly able to penetrate the container. The disinfectant solution may be hypochlorous acid or metal ion hypochlorite. The salt solution may be a predetermined volume of sterile saline solution.

21 Claims, 4 Drawing Sheets

(51) Int. Cl.
*C25B 11/12* (2006.01)
*C25B 9/06* (2006.01)

(56) References Cited

U.S. PATENT DOCUMENTS

| | | | |
|---|---|---|---|
| 5,242,595 A | 9/1993 | Morgart et al. | |
| 5,622,848 A | 4/1997 | Morrow | |
| 5,716,526 A | 2/1998 | Kelemen et al. | |
| 5,749,232 A | 5/1998 | Sauer | |
| 6,296,744 B1 | 10/2001 | Djeiranishvili et al. | |
| 6,426,066 B1 | 7/2002 | Najafi et al. | |
| 6,528,214 B1 | 3/2003 | Pliner et al. | |
| 6,551,648 B1 | 4/2003 | Goudedranche et al. | |
| 6,596,838 B1 * | 7/2003 | Pinery | C08G 73/10 204/157.76 |
| 6,632,347 B1 | 10/2003 | Buckley et al. | |
| 6,752,757 B2 | 6/2004 | Muir et al. | |
| 6,824,809 B2 | 11/2004 | Goudedranche et al. | |
| 7,090,753 B2 | 8/2006 | Sumita | |
| 7,141,262 B2 | 11/2006 | Maubois et al. | |
| 7,183,048 B2 | 2/2007 | Felkner et al. | |
| 7,276,255 B2 | 10/2007 | Selkon | |
| 7,303,660 B2 | 12/2007 | Buckley et al. | |
| 7,393,522 B2 | 7/2008 | Najafi | |
| 7,422,668 B2 | 9/2008 | Cross | |
| 7,442,288 B2 | 10/2008 | Sumita | |
| 7,828,942 B2 | 11/2010 | Cocking | |
| 8,025,784 B2 | 9/2011 | Tongiani et al. | |
| 8,062,500 B2 | 11/2011 | Sumita | |
| 8,147,444 B2 | 4/2012 | Alimi et al. | |
| 8,162,924 B2 | 4/2012 | Boyden et al. | |
| 8,173,197 B2 | 5/2012 | Aoun | |
| 8,216,173 B2 | 7/2012 | Dacey, Jr. et al. | |
| 8,277,634 B2 | 10/2012 | Chen et al. | |
| 8,282,593 B2 | 10/2012 | Dacey, Jr. et al. | |
| 8,323,252 B2 | 12/2012 | Alimi | |
| 8,343,086 B2 | 1/2013 | Dacey, Jr. et al. | |
| 8,366,652 B2 | 2/2013 | Dacey, Jr. et al. | |
| 8,414,517 B2 | 4/2013 | Dacey, Jr. et al. | |
| 8,628,028 B2 | 1/2014 | DiBello et al. | |
| 8,632,823 B2 | 1/2014 | Selkon | |
| 8,709,495 B2 | 4/2014 | Chen et al. | |
| 8,784,900 B2 | 7/2014 | Northey | |
| 8,785,713 B2 | 7/2014 | Hong et al. | |
| 8,834,445 B2 | 9/2014 | Alimi et al. | |
| 8,840,873 B2 | 9/2014 | Alimi | |
| 8,852,182 B2 | 10/2014 | Tullis et al. | |
| 8,871,278 B2 | 10/2014 | Panicheva et al. | |
| 8,877,257 B2 | 11/2014 | Goldan et al. | |
| 8,888,731 B2 | 11/2014 | Dacey, Jr. et al. | |
| 8,937,043 B2 | 1/2015 | Maubois et al. | |
| 2008/0067078 A1 | 3/2008 | Kitaori et al. | |
| 2010/0030132 A1 | 2/2010 | Niezgoda | |
| 2012/0237616 A1 | 9/2012 | Panicheva | |
| 2012/0269904 A1 | 10/2012 | Northey | |
| 2013/0256152 A1 * | 10/2013 | Creeth | C25B 1/003 205/637 |
| 2013/0261534 A1 | 10/2013 | Niezgoda | |

OTHER PUBLICATIONS

International Search Report and Written Opinion received for PCT US2016/16419 dated Apr. 14, 2016.

* cited by examiner

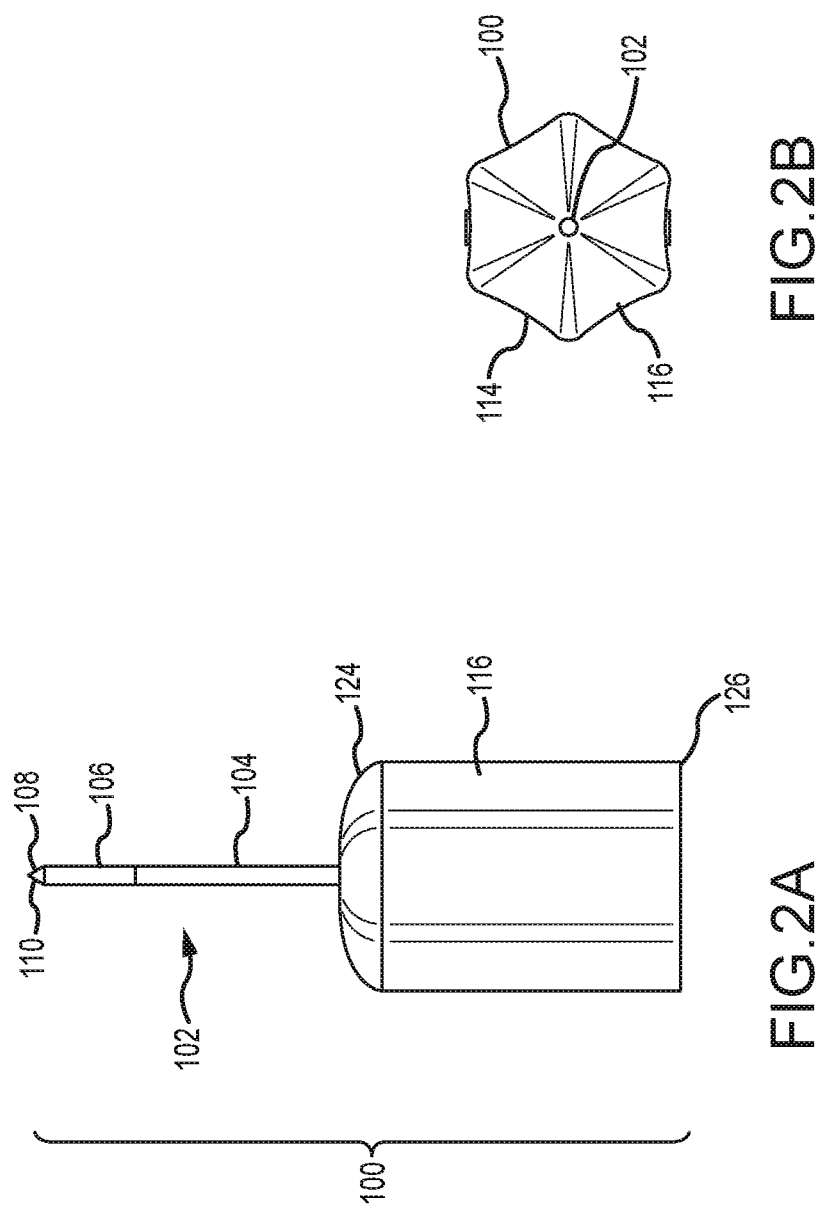

DEVICES AND METHODS FOR ELECTROLYTIC PRODUCTION OF DISINFECTANT SOLUTION FROM SALT SOLUTION IN A CONTAINER

CROSS-REFERENCE TO RELATED APPLICATION(S)

This application claims the benefit of the earlier filing date of U.S. Provisional Application 62/111,304, filed Feb. 3, 2015. The entire content of the provisional application is hereby incorporated by reference in its entirety, for any purpose.

TECHNICAL FIELD

Examples described herein generally relate to devices and methods for the electrolytic production of a disinfectant solution from a salt solution.

BACKGROUND

Electrolysis of a sodium chloride solution produces sodium hypochlorite, the active ingredient in bleach, and hypochlorous acid, a disinfectant/antiseptic/biocide used for wound cleaning, wound debridement, wound sterilization, water sanitation, and surface sterilization. Sodium hypochlorite and hypochlorous acid are each unstable and break down over time due to contact with air, sunlight, and organics. Manufactured solutions of each chemical have a short shelf life. Therefore, there is a need for on-demand production of sodium hypochlorite and hypochlorous acid to help ensure that each solution is chemically active.

BRIEF DESCRIPTION OF THE DRAWINGS

FIG. 2A is a front elevation view of a device in accordance with examples described herein.

FIG. 2B is a top elevation view of the device of FIG. 2A.

DETAILED DESCRIPTION

Figure 1B:
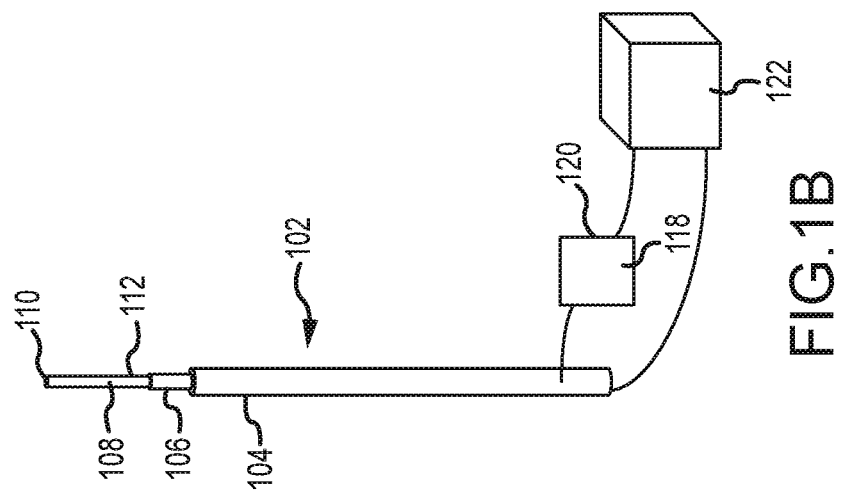
FIG. 1B is a schematic illustration of a device in accordance with examples described herein.

Certain details are set forth below to provide a sufficient understanding of embodiments of the invention. However, it will be clear to one skilled in the art that embodiments of the invention may be practiced without various of these particular details. In some instances, well-known circuits, control signals, timing protocols, and software operations have not been shown in detail in order to avoid unnecessarily obscuring the described embodiments of the invention.

One salt solution, sterile saline, has multiple uses in medicine and dentistry including intravenous infusion and flushing cavities. Users of both salt solutions and disinfectant solutions, such as medical and dental personnel and military troops in the field, currently stock or carry both types of solutions, which occupies space and increases load weight. Therefore, there is a need for a convenient and portable device for and method of producing a disinfectant solution from a readily available or readily producible salt solution. There is also a need for the device and method to operate by batch processing so the disinfectant solution can be conveniently used, including with other medical equipment such as a wound debridement system, transported, or stored.

Sterile saline is used for safe parenteral delivery of salt solutions into the body or for safe application to surfaces, such as mucous membranes and the eyes, that lead into the body. Sterile saline is often provided as a fixed volume in a sterile container. Examples of the presently disclosed devices and methods may unexpectedly transform sterile saline into a disinfectant that would be harmful or poisonous to administer into the body.

Electrolysis of a salt (sodium chloride) solution generally produces hydrogen gas at the cathode and chlorine gas at the anode. The chlorine gas disproportionates to hypochlorous acid (HClO) and sodium hypochlorite (NaClO). Sodium hypochlorite dissolved in water is the disinfectant bleach. The proportions of hypochlorous acid and sodium hypochlorite reaction products are pH dependent: at a pH of about 3 to about 7, greater than 80% of the chlorine species is maintained as hypochlorous acid; and at a pH of about 3 to about 6, greater than 97% of the chlorine species is maintained as hypochlorous acid.

Electrolysis of salt solutions is generally conducted in large-scale manufacturing facilities. The disinfectant products are shipped and stored by the recipient but the products are unstable and break down over time. In contrast, on-demand production of hypochlorous acid and sodium hypochlorite helps ensure that the disinfectant solutions are chemically active when used. On-demand production also provides flexibility in utilizing readily available salt solutions to generate disinfectant solutions.

Devices and methods described herein include examples of devices and methods for on-demand batch production of a disinfectant solution from a salt solution in a container, which may be a dosed or sealed portable container. The salt solution may have a predetermined fixed volume. For example 250 mL, 500 mL, and 1000 mL IV bags containing salt solution (e.g. sterile saline) may be used to generate a disinfectant solution in accordance with examples described herein.

Figure 1A:
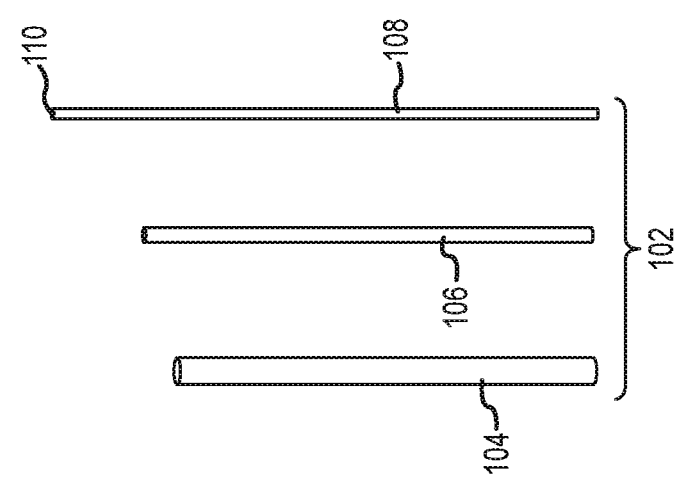
FIG. 1A is a schematic illustration of an electrode assembly of a device in accordance with examples described herein.

FIG. 1A is a schematic illustration of an electrode assembly of a device in accordance with examples described herein. The electrode assembly 102 includes a cathode 104, an anode 108, and an insulator 106. The cathode 104 may be constructed of any conductive material including, but not limited to, stainless steel, copper, and carbon. Generally, the cathode 104 may be constructed of a material useful for electrolysis. The cathode 104 may be constructed with a cavity 112 extending the length of the cathode 104. The cavity 112 may be configured to receive an insulator 106 and an anode 108. The cavity 112 may be configured to permit the flow of fluid through the cathode 104. The cathode 104 may be constructed of a needle, such as a 13-gauge, 14-gauge, 15-gauge, 16-gauge, 17-gauge, 18-gauge, or 19-gauge needle.

The anode 108 may be constructed of any conductive material including, but not limited to, titanium, copper, and carbon. Generally, the anode 108 may be constructed of a material useful for electrolysis. The conductive material may be coated with an oxide, which may be iridium oxide or ruthenium oxide. In the construction and use of the anode 108, the oxide coating may catalyze oxidation of chlorine in a salt solution and may improve coulombic efficiency of an electrolysis reaction. The anode 108 may be constructed of any grade of titanium, such as grade 1, 2, 3, or 4, or any grade of titanium alloy, such as grade 5. The anode 108 may have a diameter smaller than the diameter of the cathode 104. The smaller diameter of the anode 108 may help the anode 108 fit within the cavity 112 of the cathode 104.

The insulator 106 of the electrode assembly 102 may be constructed of a dielectric material. The dielectric material may be, for example, a temperature-stable polyimide film, such as poly (4,4'-oxydiphenylene-pyromellitimide) (Kapton®), or a heat-shrinkable plastic. In the construction and use of the electrode assembly 102, the insulator 106 may help maintain physical separation of the cathode 104 and anode 108 such that electrolysis can occur between the cathode 104 and anode 108. For example, the insulator 106 may cover or surround the anode 108 and the insulator-covered anode 108 may be positioned within the cavity 112 of the cathode 104.

The electrode assembly 102 may terminate in a tip 110. The tip 110 may be constructed such that it is able to penetrate a container 160, such as the septum of an intravenous (IV) saline bag or the lid of a plastic bottle. In some embodiments, the tip 110 may be pointed or beveled, which may help the electrode assembly 102 penetrate a container 160. The tip 110 may be positioned at a terminus of the anode 108.

The electrode assembly 102 may be any length long enough to penetrate a container wall or lid and reach the salt solution inside the container. In embodiments, the length is from about 1 cm to about 10 cm, or from about 1 cm to about 8 cm, or from about 1 cm to about 6 cm, or from about 1 cm to about 4 cm, or from about 1 cm to about 2 cm, or from about 2 cm to about 10 cm, or from about 4 cm to about 10 cm, or from about 6 cm to about 10 cm, or from about 8 cm to about 10 cm.

The electrode assembly 102 may be coated with a material that helps to change or maintain the pH of the salt solution into which the electrode assembly 102 is inserted. The coating may be hard, such as like a hard candy shell. The material may be an acidic material or buffer that helps to lower or maintain the pH of the salt solution. The buffer may be citric acid (2-hydroxypropane-1,2,3-trioic acid), which may be powdered citric acid.

In some implementations, the buffer dissolves in the salt solution and helps to maintain the pH of the salt solution at, for example, about 3 to about 7 even when the byproducts of electrolysis would otherwise raise the pH of the solution. In some implementations, the amount of buffer coated on the electrode assembly 102 helps to maintain the pH of the salt solution at about 3 to about 7 of many volumes of salt solution. In the construction and use of the device 100, a buffer amount that maintains a desired pH when inserted into a wide range of salt solution volumes helps to improve the convenience and versatility of the device 100 because a user can use one device to successfully produce disinfectant solution from, for example, many different sizes of IV saline bags.

The amount of buffer may be from about 50 mg to about 100 mg, or about 50 mg to about 95 mg, or about 50 mg to about 90 mg, or about 50 mg to about 85 mg, or about 50 mg to about 80 mg, or about 50 mg to about 75 mg, or about 55 mg to about 100 mg, or about 60 mg to about 100 mg, or about 65 mg to about 100 mg, or about 70 mg to about 100 mg, or about 75 mg to about 100 mg, or about 70 mg to about 80 mg, or about 76 mg.

The amount of salt solution buffered by the buffer-coated electrode assembly 102 may be from about 250 mL to about 1000 mL, or from about 250 mL to about 900 mL, or from about 250 mL to about 800 mL, or from about 250 mL to about 700 mL, or from about 250 mL to about 600 mL, or from about 250 mL to about 500 mL, or from about 250 mL to about 400 mL, or from about 300 mL to about 1000 mL, or from about 400 mL to about 1000 mL, or from about 500 mL to about 1000 mL, or from about 600 mL to about 1000 mL, or from about 700 mL to about 1000 mL, or from about 800 mL to about 1000 mL.

The electrode assembly 102 may be coated with an indicator dye. The indicator dye may be any chemical that is capable of revealing the presence of a disinfectant solution. The dye may be methyl violet, which may be powdered methyl violet. The dye may be combined with a buffer, such as citric acid. The dye may be colored and may denature in the presence of hypochlorous acid, which may cause the dye to turn a different color or turn clear. Accordingly, once the disinfectant solution is produced, the fluid in the bag may have a color change—for example going from a red saline solution to a clear disinfectant solution.

FIG. 1B is a schematic illustration of a device in accordance with examples described herein. The electrolysis device 100 may include an electrode assembly 102, a circuit board 118, and a power switch 120. The electrolysis device 100 may also include a battery 122. Each of the circuit board 118, power switch 120, and battery 122 may be associated with a base 114 as shown in FIG. 2A.

FIGS. 2A and 2B are elevation views of an electrolysis device in accordance with examples described herein. The electrolysis device 100 may include a base 114. The base 114 may be any shape, such as rectangular or cylindrical. With reference to FIGS. 2A and 2B, the base 114 may be hexagonal. The base 114 may receive the electrode assembly 102 in a top side 124 of the base 114. The base 114 may be configured to permit the flow of fluid through the base 114 to the electrode assembly 102. The base 114 may provide a surface or area to grip or hold the device 100. The base 114 may include a housing 116, which may partially or completely surround components of the base 114.

The circuit board 118 may be enclosed within the housing 116. The circuit board 118 may be coupled to one or both of the electrode assembly 102 and power switch 120. In the construction and use of the electrolysis device 100, the circuit board 118 may permit variation of the electrolytic parameters to vary the dose of electrons generated. The parameters may be varied to either increase or decrease the final amount or concentration of disinfectant solution produced. The circuit board 118 may also permit variation in applied potential or limiting current.

In embodiments, the applied current is from about 0.01 mA to about 1000 mA, or from about 0.01 mA to about 900 mA, or from about 0.01 mA to about 800 mA, or from about 0.01 mA to about 700 mA, or from about 0.01 mA to about 600 mA, or from about 0.01 mA to about 500 mA, or from about 0.01 mA to about 400 mA, or from about 0.01 mA to about 300 mA, or from about 0.01 mA to about 200 mA, or from about 0.01 mA to about 100 mA, or from about 0.1 mA to about 1000 mA, or from about 1 mA to about 1000 mA, or from about 100 mA to about 1000 mA, or from about 200 mA to about 1000 mA, or from about 300 mA to about 1000 mA, or from about 400 mA to about 1000 mA, or from about 500 mA to about 1000 mA, or from about 600 mA to about 1000 mA, or from about 700 mA to about 1000 mA, or from about 800 mA to about 1000 mA, or from about 100 mA to about 500 mA. In embodiments, the applied current varies with time of application and volume of salt solution to which the current is applied.

In embodiments, the voltage applied is from about 0.5 V to about 9 V, or from about 0.5 V to about 8 V, or from about 0.5 V to about 8 V, or from about 0.5 V to about 6 V, or from about 0.5 V to about 5 V, or from about 0.5 V to about 4 V, or from about 0.5 V to about 3 V, or from about 0.5 V to about 2 V, or from about 1 V to about 9 V, or from about 2 V to about 9 V, or from about 3 V to about 9 V, or from about 4 V to about 9 V, or from about 5 V to about 9 V, or from about 6 V to about 9 V, or from about 7 V to about 9 V, or from about 2 V to about 3 V.

The base 114 may include a power switch 120, which may he coupled to the circuit board 118. Actuating the power switch 120 may control power application to the device 100. In some embodiments, when power is provided to the device 100, electrolysis begins at the electrode assembly 102. The power switch 120 may be a push button, slide, or other mechanism that permits both an on and an off mode of the device 100. The power switch 120 may be positioned anywhere in or on the base 114, such as on the exterior of the housing 116. For example, with reference to FIG. 3, the power switch 120 is a push button and is positioned at a bottom side 126 of the base 114.

The device 100 may be powered by direct or alternating current. The device 100 may be powered by a battery 122, such as a 9V battery. The battery 122 may be enclosed by the housing 116. Additionally or alternatively, the device 100 may be plugged in to an electrical outlet.

In some embodiments, the base 114 includes a timer. The timer may be positioned within the housing 116. In the construction and use of the device 100, the timer permits operating the device 100 for a set period of time. In embodiments, the time is from about 1 second to about 60 minutes, or from about 1 minute to about 60 minutes, or from about 1 minute to about 50 minutes, or from about 1 minute to about 40 minutes, or from about 1 minute to about 30 minutes, or from about 1 minute to about 20 minutes, or from about 1 minute to about 10 minutes, or from about 1 minute to about 5 minutes, or from about 5 minutes to about 60 minutes, or from about 10 minutes to about 60 minutes, or from about 20 minutes to about 60 minutes, or from about 30 minutes to about 60 minutes, or from about 40 minutes to about 60 minutes, or from about 50 minutes to about 60 minutes, or from about 5 minutes to about 25 minutes.

In some embodiments, the base 114 includes a pH meter. The pH meter may be positioned within the housing 116. The anode 102 may serve as a reference electrode for the pH meter. In the construction and use of the device 100, the pH meter may be used to determine or monitor the pH level of the salt solution or the disinfectant solution produced from the salt solution. Data from the pH meter may allow a user of the device 100 to change the pH of a solution to, or maintain the pH of a solution at, a desired pH. For example, the desired pH of a salt solution may be approximately 4 to 6 and data from the pH meter may demonstrate that the pH is higher than 6. A user may then decrease the pH of the salt solution.

In some embodiments, the base 114 includes a chlorometer. In the construction and use of the device 100, the chlorometer may determine or monitor the active chlorine levels in the salt solution or the disinfectant solution produced from the salt solution. Data from the chlorometer may allow a user of the device 100 to determine the chlorine levels of a solution, such as in order to evaluate whether hypochlorous acid or sodium hypochlorite is being or has been produced by electrolysis of the salt solution.

In some embodiments, the base 114 includes chlorine paper. In the construction and use of the device 100, the chlorine paper may be used to determine or monitor the active chlorine levels in the salt solution or the disinfectant solution produced from the salt solution. Data from the chlorine paper may allow a user of the device 100 to determine the chlorine levels of a solution, such as in order to evaluate whether hypochlorous acid or sodium hypochlorite is being or has been produced by electrolysis of the salt solution.

In some embodiments, the base 114 includes an indicator dye or a port for receiving an indicator dye. The indicator dye may be any indicator dye described above. In some embodiments, the indicator dye flows from the base 114 through a cavity 112 in the cathode 104 into the container 160 comprising the salt solution or disinfectant solution. Accordingly, once the disinfectant solution is produced, the fluid in the bag may have a color change—for example going from a red saline solution to a clear disinfectant solution.

In some embodiments, the base 114 includes a pH buffer or a port for receiving a pH buffer. The pH buffer may be any chemical that is capable of changing the pH of a solution. In some embodiments, the pH buffer is acidic or is an acid, such as citric acid, and decreases the pH of the salt solution or disinfectant solution. In some embodiments, the pH buffer is basic or is a base and increases the pH of the salt solution or disinfectant solution. In the construction and use of the device 100, the pH buffer may help to direct, such as by raising or lowering the pH of the salt solution, the disinfectant solution that is produced. For example, hypochlorous acid may be the predominant species produced from electrolysis of a salt solution having a pH from about 3 to about 7 or from about 4 to about 6. A pH buffer may be added to the salt solution to change the pH to about 3 to about 4 such that electrolysis of the salt solution yields a disinfectant solution comprising predominantly hypochlorous acid. In some embodiments, the pH buffer flows from the base 114 through a cavity 112 in the cathode 104 into the container 160 comprising the salt solution or disinfectant solution.

Figure 4:
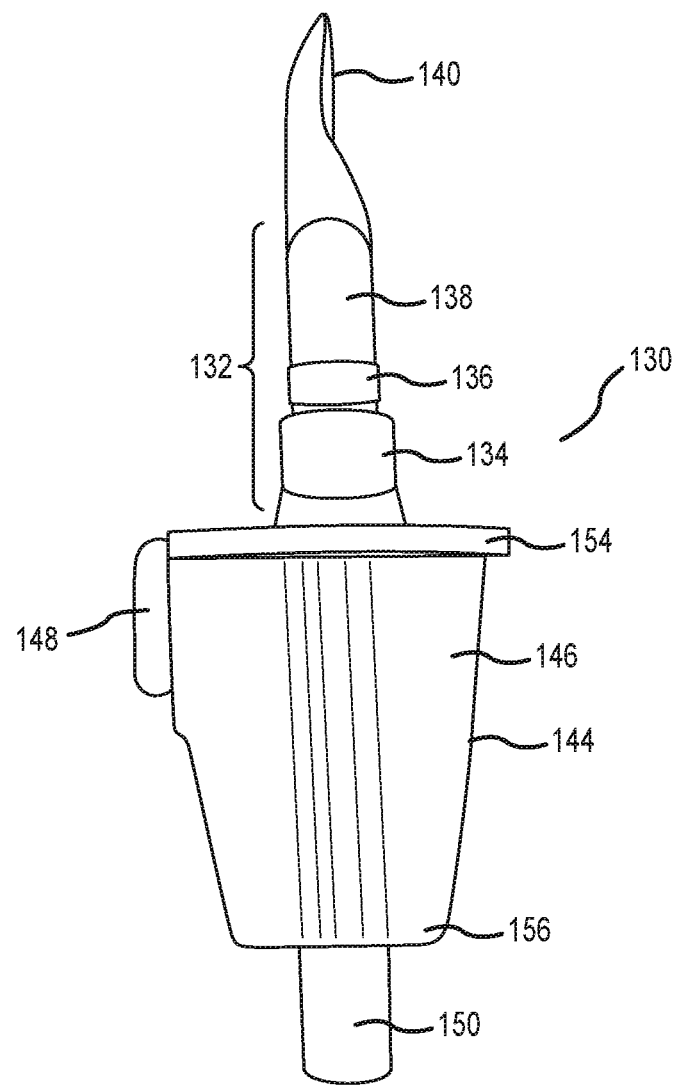
FIG. 4 is a front isometric view of a device in accordance with examples described herein.

FIG. 4 is a front isometric view of a device 200 in accordance with examples described herein. The device 200 may include an electrode assembly 132 and a base 144. The electrode assembly 132 may include a cathode 134, an anode 138, and a separator 136. The cathode 134 may be constructed of any conductive material including, but not limited to, stainless steel, copper, and carbon. The cathode 134 may be constructed with a cavity extending the length of the cathode 134. The cavity may be configured to permit the flow of fluid through the cathode 134.

The anode 138 may be constructed of any conductive material including, but not limited to, titanium, copper, and carbon. The conductive material may be coated with an oxide, which may be iridium oxide or ruthenium oxide. In the construction and use of the anode 138, the oxide coating may catalyze oxidation of chlorine in a salt solution and may improve coulombic efficiency of an electrolysis reaction. The anode 138 may be constructed of any grade of titanium, such as grade 1, 2, 3, or 4, or any grade of titanium alloy, such as grade 5. The anode 138 may be constructed with a cavity extending the length of the anode 138. The cavity may be configured to permit the flow of fluid through anode 138.

The separator 136 of the electrode assembly 132 may be constructed of a dielectric material. The dielectric material may be, for example, a temperature-stable polyimide film, such as poly (4,4'-oxydiphenylene-pyromellitimide) (Kapton®), or a heat-shrinkable plastic. In the construction and use of the electrode assembly 132, the separator 136 may help maintain physical separation of the cathode 134 and anode 138 such that electrolysis can occur between the cathode 134 and anode 138. For example, the separator 136 may be positioned between the cathode 134 and anode 138. The separator 136 may be constructed with a cavity extending the length of the separator 136. The cavity may be configured to permit the flow of fluid through separator 136.

The electrode assembly 132 may terminate in a tip 140. The tip 140 may be constructed such that it is able to penetrate a container 160, such as the septum of an intravenous (IV) saline bag or the lid of a plastic bottle. In some embodiments, the tip 140 may be pointed or beveled, which may help the electrode assembly 132 penetrate a container 160. The tip 110 may be positioned at a terminus of the anode 138.

As described above for the electrode assembly 102, the electrode assembly 132 may be coated with a material that helps to change or maintain the pH of the salt solution into which the electrode assembly 132 is inserted.

In embodiments, the electrode assembly 132 has a shape similar to a spike that is inserted into an IV bag and that permits the flow of fluid from an IV bag into an IV line or tube. The electrode assembly 132 may be any length long enough to penetrate a container wall or lid and reach the salt solution inside the container. In embodiments, the length is from about 1 cm to about 10 cm, or from about 1 cm to about 8 cm, or from about 1 cm to about 6 cm, or from about 1 cm to about 4 cm, or from about 1 cm to about 2 cm, or from about 2 cm to about 10 cm, or from about 4 cm to about 10 cm, or from about 6 cm to about 10 cm, or from about 8 cm to about 10 cm.

The base 144 may receive the electrode assembly 132 in a top side 154 of the base 114. The base 144 may include a housing 146. The base 144 may also include a circuit board, a power switch, and a battery as described above for the base 114. The base 144 may also include any one or more of a timer, pH meter, chlorometer, chlorine paper, indicator dye, and pH buffer as described above for the base 114.

In embodiments, the base 144 includes a clamp 148. The clamp 148 may be positioned on the base 144, such as adjacent the housing 146 near the top side 154 of the base 144. In the construction and use of the device 200, the clamp 148 may help to control the flow of fluid through the device 200, such as from a container 160, through the device 200, into a port 150, and into an IV line or tube. In the construction and use of the device 200, it may permit the flow of fluid similarly to a conventional spike that permits fluid transfer out of an IV bag. The port 150 may be positioned adjacent the bottom side 156 of the base 144.

In some embodiments, the electrolysis device 100, 200 is configured to be removable from the container 160 after use in some embodiments, the device 100, 200 is configured to remain in the container 160 after use. In some embodiments, the device 100, 200 is reusable. In some embodiments, the device 100, 200 is portable, such as by being lightweight and small enough to fit in a clothing pocket.

Salt solutions compatible with the devices and methods disclosed herein may include from about 0.3% w/v to about 6% w/v of salt, or from about 0.3% w/v to about 5% w/v, or from about 0.3% w/v to about 4% w/v, or from about 0.3% w/v to about 3% w/v, or from about 0.3% w/v to about 2% w/v, or from about 0.3% w/v to about 1% w/v, or from about 1% w/v to about 6% w/v, or from about 2% w/v to about 6% w/v, or from about 3% w/v to about 6% w/v, or from about 4% w/v to about 6% w/v, or from about 0.5% w/v to about 5% w/v, or from about 0.5% w/v to about 1% w/v, or from about 0.8% w/v to about 1% w/v, or about 0.9% w/v of salt.

The pH of the salt solution may be, or may be adjusted to, from about 2 to about 8, or from about 2 to about 7, or from about 2 to about 6, or from about 2 to about 5, or from about 2 to about 4, or from about 3 to about 8, or from about 4 to about 8, or from about 5 to about 8, or from about 6 to about 8, or from about 3 to about 6, or from about 4 to about 6.

In some embodiments, the salt solution is a sterile salt solution. In some embodiments, the salt solution has a set or predetermined volume.

In some embodiments, the salt solution is a sodium chloride solution. In some embodiments, the salt solution is a 0.9% sodium chloride solution with a pH of 3 to 6. In some embodiments, the salt solution is a sterile 0.9% sodium chloride solution with a pH of 3 to 6.

Containers 160 compatible with the devices and methods disclosed herein may include any vessel capable of storing a salt solution. For example, the containers 160 may be plastic bags, bottles, or jugs. In some embodiments, the container 160 is sealed. In some embodiments, the salt solution within the container 160 is sterile. The container 160 may be an IV bag of saline or a bottle of saline, either of which may be sterile saline.

The container 160 may have any volume. In embodiments, the volume is from about 10 mL to about 2 L, or from about 10 mL to about 1.5 L, or from about 10 mL to about 1 L, or from about 10 mL to about 500 mL, or from about 10 mL to about 250 mL, or from about 10 mL to about 100 mL, or from about 10 mL to about 50 mL, or from about 50 mL to about 2 L, or from about 100 mL to about 2 L, or from about 250 mL to about 2 L, or from about 500 mL to about 2 L, or from about 1 L to about 2 L.

In some embodiments, the disinfectant solution is produced by a batch process from a container 160 of salt solution.

In some embodiments, the device 100, 200 is integrated into the container 160.

Electrolysis of the salt solutions described herein may produce disinfectant solutions. The disinfectant solution may be hypochlorous acid, metal ion hypochlorite, or a combination thereof. The type of disinfectant solution produced may be selected or changed by selecting or changing any one or more of the pH of the salt solution, the pH of the disinfectant solution, the duration of time of application of electrolysis, and the electrolysis current.

The concentration of the disinfectant solution may be from about 0.01 ppm to about 5000 ppm, or from about 0.01 ppm to about 4000 ppm, or from about 0.01 ppm to about 3000 ppm, or from about 0.01 ppm to about 2000 ppm, or from about 0.01 ppm to about 1000 ppm, or from about 0.01 ppm to about 800 ppm, or from about 0.01 ppm to about 600 ppm, or from about 0.01 ppm to about 400 ppm, or from about 0.01 ppm to about 200 ppm, or from about 0.01 ppm to about 100 ppm, or from about 0.1 ppm to about 5000 ppm, or from about 1 ppm to about 5000 ppm, or from about 10 ppm to about 5000 ppm, or from about 100 ppm to about 5000 ppm, or from about 200 ppm to about 5000 ppm, or from about 400 ppm to about 5000 ppm, or from about 600 ppm to about 5000 ppm, or from about 800 ppm to about 5000 ppm, or from about 1000 ppm to about 5000 ppm, or from about 2000 ppm to about 5000 ppm, or from about 3000 ppm to about 5000 ppm, or from about 0.01 ppm to about 1000 ppm, or from about 50 ppm to about 500 ppm, or from about 100 ppm to about 350 ppm.

The disinfectant solution produced by the methods disclosed herein may he used immediately after production or may be stored. The disinfectant solution produced by the methods disclosed herein may be used as, for example, a disinfecting agent, a bleaching agent, a biocide, or an antiseptic. The disinfectant solution produced by the methods disclosed herein may be used to, for example, wash wounds, debride wounds, sterilize wounds, sterilize surfaces, or sterilize devices.

Sterile saline is used for safe parenteral delivery of salt solutions into the body or for safe application to surfaces, such as mucous membranes and the eyes, that lead into the body. Examples of the presently disclosed devices and methods may unexpectedly transform sterile saline into a disinfectant that would be harmful or poisonous to administer into the body.

In some implementations, a colored dye is added to the container to provide a clear signal to a user or observer that the bag contents are a harmful disinfectant solution. The dye may be an indicator dye. Once the disinfectant solution is produced, the fluid in the bag may have a color change—for example going from a clear saline solution to a purple disinfectant solution.

Example methods described herein produce a disinfectant solution (e.g. hypochlorous acid) from a salt solution in a container. Each of the disinfectant solution, salt solution, and container may be any disinfectant solution, salt solution, and container, respectively, described above. Power is supplied to the device 100, 200, which may be any device 100, 200 described above. Supplying power to the device 100, 200, such as to the electrode assembly 102, 132 may initiate electrolysis of the salt solution to produce a disinfectant solution.

Electrolysis conditions may be varied based on the amount of current applied, the time of application of the current, and the volume of salt solution to which the current is applied. For example, about 300 ppm of disinfectant solution may be obtained by electrolyzing 500 mL of salt solution for 12 minutes at 300 mA. About 200 ppm of disinfectant solution may be obtained by electrolyzing 500 mL of salt solution for 15 minutes at 150 mA. About 60 ppm of disinfectant solution may be obtained by electrolyzing 1 L of salt solution for 40 minutes at 300 mA. About 20 ppm of disinfectant solution may be obtained by electrolyzing 1 L of salt solution for 15 minutes at 400 mA. Accordingly, an electrolysis time and current may be selected to yield a desired concentration of the disinfectant solution.

Figure 3:
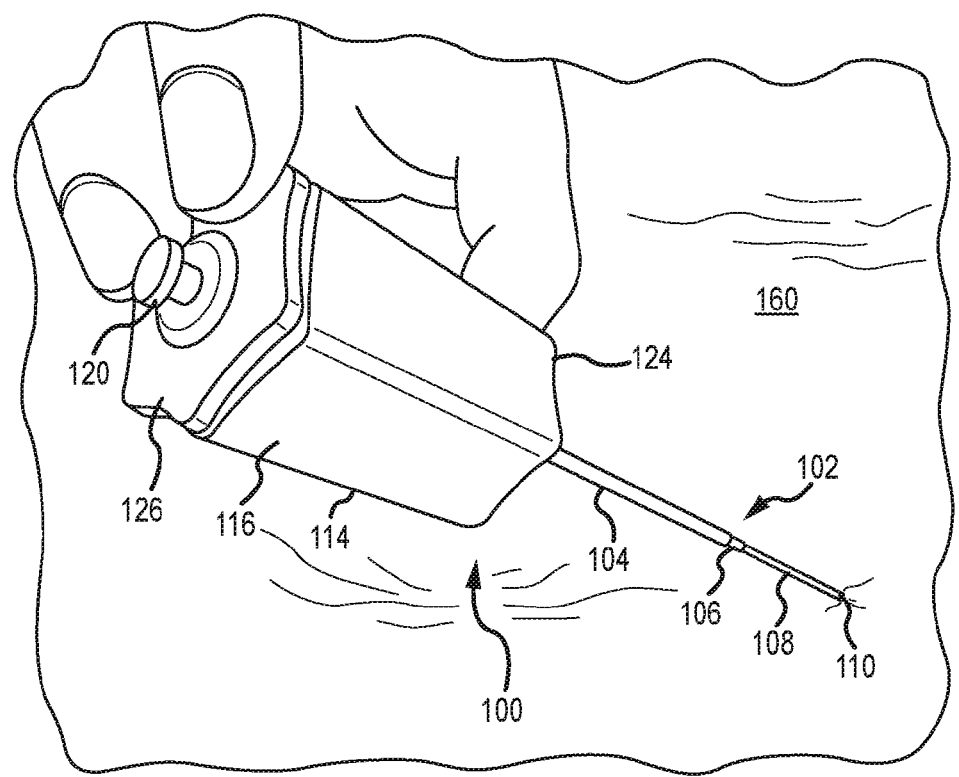
FIG. 3 is a front right isometric view of a device penetrating a container in accordance with examples described herein.

In some embodiments, and with reference to FIG. 3, a wall or the lid of the container 160 is penetrated by the device's 100 electrode assembly 102, such as by the tip 110. The container 160 may remain sealed or closed when the device 100 is inserted into the container 160. The contents of the container 160 may remain sterile when the device 100 is inserted into the container 160.

In some embodiments, the pH of the salt solution or disinfectant solution is changed to or maintained at a desired pH. For example, a pH buffer may be added to the salt solution to change the pH to about 3 to about 4 such that electrolysis of the salt solution yields a disinfectant solution comprising predominantly hypochlorous acid. As another example, the electrode assembly 102, 132 may be coated with a material, such as citric acid, that helps to change or maintain the pH of the salt solution. In some embodiments, a pH meter is provided with the device 100, 200 and helps to monitor the pH of the salt solution or the disinfectant solution.

In some embodiments, the method includes batch production of a disinfectant solution in a container. When electrolysis commences, the concentration (ppm) of disinfectant solution is low. As the reaction proceeds, the concentration of disinfectant solution increases over time. In some embodiments, a portion of the disinfectant solution is withdrawn from the container while electrolysis is still being performed (e.g. through another septum of an IV bag or through the spike forming the electrode assembly in accordance with examples described herein). The concentration of disinfectant solution may increase when the volume of the solution decreases by withdrawing solution before electrolysis is complete.

In some implementations, the batch production of disinfectant solution is from a container of a fixed volume of sterile saline. The sterile saline, which can be used for safe parenteral delivery of salt solutions into the body or for safe application to surfaces, such as mucous membranes and the eyes, that lead into the body, may be unexpectedly transformed into a disinfectant that would be harmful or poisonous to administer into the body.

After production of the disinfectant solution, the device 100, 200 may be left in or removed from the container 160. In some implementations, a removed device 100, 200 may be reinserted in the same container to produce more disinfectant solution in the container. In some implementations, the device 100, 200 is reused with another container 160 of salt solution.

By way of example, but not limitation, the electrolytic device 100 of FIGS. 1-3 may be used to produce a disinfectant solution from a salt solution in a container according to the following procedure. The electrode assembly 102 of the device 100 is inserted at least partially into the septum of a sterile IV saline (0.9%, pH 5) bag 160. The device 100 is turned on by actuating the power switch 120 and is held in place for 5 minutes while electrolysis occurs between the anode 108 and cathode 104 of the electrode assembly 102 to produce hypochlorous acid (97%)/sodium hypochlorite from the saline solution. The device 100 is then removed from the septum. The disinfectant solution (e.g. hypochlorous acid/sodium hypochlorite) may be used to disinfect, clean, or debride a wound using manual irrigation or by fluid connection to a debridement tool. Accordingly, the disinfectant solution may be made in a container (e.g. an IV bag) that is also used to dispense the disinfectant solution to a wound or another tool (e.g. through connective tubing).

By way of example, hut not limitation, the electrolytic device 100 of FIGS. 1-3 may be used to produce a disinfectant solution from a salt solution in a container according to the following procedure. The electrode assembly 102 of the device 100 is inserted through the plastic lid of a bottle 160 of sterile saline (0.9%, pH 5). Hypochlorous acid/sodium hypochlorite is produced according to the method described above. The hypochlorous acid/sodium hypochlorite may be used as a disinfectant in endodontic surgery.

By way of example, but not limitation, the electrolytic device 100 of FIGS. 1-3 may be used to produce a disinfectant solution from a salt solution in a container according to the following procedure. The device 100 is transported by soldiers into a military combat situation in which chemical or biological weapons are employed. Water (1 L) and salt (9 g) are combined in a plastic jug. The device 100 is inserted through the lid or wall of the jug and the citric acid of a buffer-coated electrode assembly 102 dissolves in the salt solution, which lowers the pH to approximately 3. Hypochlorous acid/sodium hypochlorite is produced according to the method described above. The hypochlorous acid/sodium hypochlorite may be used to destroy chemical or biological contaminants on personnel or equipment.

By way of example, but not limitation, the electrolytic device 100 of FIGS. 1-3 may be used to produce a disinfectant solution from a salt solution in a container according to the following procedure. The device 100 is transported by hikers on a camping trip. Water (1 L) and salt (9 g) are combined in a plastic jug. The device 100 is inserted through the lid or wall of the jug. Hypochlorous acid/sodium hypochlorite is produced according to the method described above. One hundred milliliters of the solution is added 1 L of river water to make it potable by killing microorganisms.

By way of example, but not limitation, the electrolytic device 130 of FIG. 4 may be used to produce a disinfectant solution from a salt solution in a container according to the following procedure. The electrode assembly 132 of the device 130 is inserted at least partially into the septum of a sterile IV saline (0.9%, pH 5) bag with the clamp 148 in the closed position. The device 130 is turned on by actuating a power switch and is held in place for 5 minutes while electrolysis occurs between the anode 138 and cathode 134 of the electrode assembly 132 to produce hypochlorous acid (97%)/sodium hypochlorite from the saline solution. The clamp 148 is then turned to the open position to allow the hypochlorous acid (97%)/sodium hypochlorite to flow through the port 150 by fluid connection to a debridement tool.

From the foregoing it will be appreciated that, although specific embodiments of the invention have been described herein for purposes of illustration, various modifications may be made without deviating from the spirit and scope of the invention.

What is claimed is:

1. A device for producing a disinfectant solution in a closed container, the device comprising:
   an electrode assembly comprising:
      an anode,
      a cathode, and
      an insulator positioned between the anode and cathode; and
   a base comprising:
      a housing,
      a circuit board coupled to the electrode assembly, and
      a power switch coupled to the circuit board and configured to control power application to the electrode assembly;
   wherein
      the container comprises a fixed volume of sterile 0.3-6% w/v salt solution; and
      at least one of the anode and the cathode of the electrode assembly is configured to form a breach in a wall of the closed container to produce, inside the closed container, hypochlorous acid from the salt solution responsive to the power application to the electrode assembly.

2. The device of claim 1, wherein the electrode assembly terminates in a beveled tip.

3. The device of claim 1, wherein the cathode is a needle comprised of a conductive material selected from stainless steel, copper, and carbon.

4. The device of claim 1, wherein
   the anode is comprised of a conductive material selected from titanium, copper, and carbon; and
   the material is coated with an oxide selected from iridium oxide and ruthenium oxide.

5. The device of claim 1, wherein the insulator comprises a dielectric material selected from a temperature-stable polyimide film and a heat-shrinkable plastic.

6. The device of claim 1, wherein the electrode assembly provides a current of about 0.01 mA to about 1000 mA.

7. The device of claim 1, wherein the container is a bag for intravenous administration of the saline solution.

8. The device of claim 1, wherein the electrode assembly is coated in citric acid.

9. The device of claim 1, wherein the base further comprises one or more of a battery, timer, pH meter, chlorometer, chlorine paper, indicator dye, and pH buffer.

10. The device of claim 1, wherein the device is configured to change the pH level of the salt solution to about 3 to about 7.

11. The device of claim 1, wherein the device is configured to determine or change the chlorine level of the salt solution or disinfectant solution.

12. The device of claim 1, wherein the closed container is sealed.

13. A method comprising:
   forming a breach in a wall of a closed container of sterile sodium chloride solution with at least an anode or a cathode of an electrode assembly;
   supplying power to the electrode assembly; and
   electrolyzing the sodium chloride solution responsive to the power, to generate a disinfectant solution in the closed container.

14. The method of claim 13, wherein the sodium chloride solution is sterile saline solution.

15. The method of claim 13, wherein the container is a bag for intravenous administration of the sodium chloride solution.

16. The method of claim 13, wherein the pH of the sodium chloride solution is maintained at pH 4-6.

17. The method of claim 13, wherein the disinfectant solution is hypochlorous acid or metal ion hypochlorite.

18. The method of claim 17, wherein the hypochlorous acid or metal ion hypochlorite is produced at 0.1 ppm to 5000 ppm.

19. The method of claim 18, wherein the hypochlorous acid or metal ion hypochlorite is produced at 100 ppm to 350 ppm.

20. The method of claim 13, wherein the disinfectant solution is produced in a batch process.

21. The method of claim 13, further comprising determining or changing the pH level of the salt solution or disinfectant solution.

* * * * *